(12) United States Patent
Zhang et al.

(10) Patent No.: US 11,748,927 B2
(45) Date of Patent: Sep. 5, 2023

(54) METHOD AND SYSTEM FOR SYNTHESIZING REAL-TIME IMAGE BY USING OPTICAL SURFACE MOTION SIGNALS

(71) Applicant: BEIJING CANCER HOSPITAL(PEKING UNIVERSITY CANCER HOSPITAL), Beijing (CN)

(72) Inventors: Yibao Zhang, Beijing (CN); Chenguang Li, Beijing (CN); Yuliang Huang, Beijing (CN); Hao Wu, Beijing (CN); Hongjia Liu, Beijing (CN)

(73) Assignee: BEIJING CANCER HOSPITAL(PEKING UNIVERSITY CANCER HOSPITAL), Beijing (CN)

( * ) Notice: Subject to any disclaimer, the term of this patent is extended or adjusted under 35 U.S.C. 154(b) by 304 days.

(21) Appl. No.: 17/037,591

(22) Filed: Sep. 29, 2020

(65) Prior Publication Data
US 2022/0020189 A1   Jan. 20, 2022

Related U.S. Application Data

(63) Continuation of application No. PCT/CN2020/102208, filed on Jul. 15, 2020.

(51) Int. Cl.
*G06K 9/00* (2022.01)
*G06T 11/60* (2006.01)
(Continued)

(52) U.S. Cl.
CPC ............ *G06T 11/60* (2013.01); *A61N 5/1039* (2013.01); *G06T 7/38* (2017.01); *G16H 20/40* (2018.01);
(Continued)

(58) Field of Classification Search
CPC ....... G06T 11/60; G06T 7/38; G06T 2200/04; G06T 2207/10076; G06T 2207/20081;
(Continued)

(56) References Cited

U.S. PATENT DOCUMENTS 10,688,320 B2 * 6/2020 Voronenko ........... A61N 5/1065
2006/0074292 A1   4/2006 Thomson et al.
(Continued)

FOREIGN PATENT DOCUMENTS

CN   101623198 A   1/2010
CN   101628154 A   1/2010
(Continued)

*Primary Examiner* — Xin Jia
(74) *Attorney, Agent, or Firm* — Bayramoglu Law Offices LLC (57) ABSTRACT

A system for synthesizing a real-time image by using optical surface motion signals includes: an acquisition unit configured to acquire an image of a patient before treatment and real-time optical surface data of the patient during treatment; and a synthesis unit configured to synthesize the acquired image of the patient before treatment and the real-time optical surface data of the patient during treatment into a real-time image that is synchronized with a change of the optical surface motion signals according to a certain mapping relationship. The synthesized real-time image achieves precise, real-time, non-invasive, visual dynamic tracking of the moving target volumes without concomitant dose during radiotherapy on the existing traditional accelerator platform.

18 Claims, 5 Drawing Sheets

Acquiring an image of a patient before treatment and real-time optical surface data of the patient during treatment

↓

Synthesizing the acquired image of the patient before treatment and the real-time optical surface data of the patient during treatment into a real-time image synchronized with a change of the optical surface motion signal according to a certain mapping relationship (51) Int. Cl.
*G06T 7/38* (2017.01)
*G16H 20/40* (2018.01)
*G16H 50/50* (2018.01)
*G16H 30/20* (2018.01)
*G16H 50/20* (2018.01)
*G16H 30/40* (2018.01)
*A61N 5/10* (2006.01)

(52) U.S. Cl.
CPC .............. *G16H 30/20* (2018.01); *G16H 30/40* (2018.01); *G16H 50/20* (2018.01); *G16H 50/50* (2018.01); *G06T 2200/04* (2013.01); *G06T 2207/10076* (2013.01); *G06T 2207/20081* (2013.01); *G06T 2207/20084* (2013.01); *G06T 2207/20221* (2013.01); *G06T 2210/41* (2013.01)

(58) Field of Classification Search
CPC . G06T 2207/20084; G06T 2207/20221; G06T 2210/41; G06T 7/30; G06T 11/005; A61N 5/1039; A61N 5/1049; A61N 5/1067; A61N 5/1037; G16H 20/40; G16H 30/20; G16H 30/40; G16H 50/20; G16H 50/50; G16H 50/30; G16H 40/67; G06N 3/0454; G06N 3/08

See application file for complete search history.

(56) References Cited

U.S. PATENT DOCUMENTS

2017/0014645 A1* 1/2017 Foo ..................... A61B 5/0035
2020/0160972 A1* 5/2020 Bériault ............... G06N 3/0454

FOREIGN PATENT DOCUMENTS

| CN | 101972515 A | 2/2011 |
| CN | 110490851 A | 11/2019 |
| CN | 110974372 A | 4/2020 |

* cited by examiner

FIG. 1

Acquiring an image of a patient before treatment and real-time optical surface data of the patient during treatment Synthesizing the acquired image of the patient before treatment and the real-time optical surface data of the patient during treatment into a real-time image synchronized with a change of the optical surface motion signal according to a certain mapping relationship

METHOD AND SYSTEM FOR SYNTHESIZING REAL-TIME IMAGE BY USING OPTICAL SURFACE MOTION SIGNALS

CROSS REFERENCE TO THE RELATED APPLICATIONS

This application is the continuation application of International Application No. PCT/CN2020/102208, filed on Jul. 15, 2020.

TECHNICAL FIELD

The present invention relates to the technical field of radiotherapy equipment, in particular to a method and system for synthesizing a real-time image by using optical surface motion signals.

BACKGROUND

The rapid increase in the incidence of malignant tumors and the number of patients has caused a heavy burden on China's social and economic development and health care system. Radiotherapy, as one of the main anti-cancer methods, can kill a tumor by delivering a precise dosage of lethal radiation to the targeted tumor, while protecting the adjacent normal tissues by forming a rapid dose fall-off at the target volume edges via advanced technology such as intensity modulation. Off-target radiation is one of the primary causes of tumor control failure and vital organ damage. Image-guided radiation therapy (IGRT), although has greatly improved the treatment accuracy by reducing the positioning error of patients, real-time monitoring of moving target volumes during radiotherapy remains a technical bottleneck that needs to break through, and still is a common problem in the interdisciplinary fields of science, engineering, medicine and information technology.

Respiratory motion is the main risk of off-target radiation dose in thoracic and abdominal radiotherapy. The amplitude and frequency of respiratory motion are comprehensively determined by many factors, such as patient's gender, age, mental state, whether the patient has any underlying diseases, as well as the radiotherapy position fixation devices and the respiratory motion management measures, etc. These complex individual differences cause uncertainties in determining the mode of an individual's respiratory motion. The influence on the traction deformation and motion trajectory of the tumor is the main threat to the precise delivery of the thoracic and abdominal radiotherapy dose. In severe cases, insufficient irradiation in the target volume may cause the tumor to recur and metastasize, and/or seriously damage the normal organs for accidentally entering the high dose area of the radiation field, which threaten the patient's life. Currently, free breathing pattern is still the first choice for more radiotherapy patients because technologies such as breath holding therapy and active breathing coordinator (ABC) have high requirements for patients' compliance and tolerance. To avoid missed exposure of moving target volumes, presently, the routine clinical method is to evaluate the law of the motion amplitude of the target volume in the preparation stage of radiotherapy, and expand the radiation range by extending the clinical target volume (CTV) outside a certain margin to form an internal target volume (ITV). However, as the amplitude of motion increases, the exponentially increasing ITV volume will contain more normal tissues. Radiation damage caused by irradiation of adjacent normal tissues is not conducive to the protection of patients' quality of life, and also restricts an increased target prescribed dose for improving the curative effect.

Respiratory motion can change the position and shape of thoracic and abdominal tumors, which may result in off-target radiotherapy dose to cause recurrence or normal organ damage. The simulation four-dimensional computed tomography (4D CT) and Magnetic Resonance Imaging (MRI), as well as the traditional 4D cone-beam CT (CBCT) with guided positioning before treatment, cannot reflect the real-time dynamics of the target volume during the treatment. Moreover, external indirect signals such as respiratory gating and optical surface signals during the treatment cannot directly demonstrate the internal structures. Additionally, real-time fluoroscopy imaging will increase the risk of radiation, and magnetic resonance (MR) accelerators that have not yet been popularized are restricted in price and compatibility. Therefore, the development of universal real-time imaging technology based on standard platforms has great scientific significance and clinical value.

In order to balance the risk of off-target and the protection of normal tissue, there is an urgent clinical need to reduce the safety margin of ITV by means of, for example, image guidance, respiratory gating, and target tracking. The technical problem that has yet to be solved is how to perform real-time, non-invasive, and visual monitoring of the internal moving target volumes.

SUMMARY

To overcome the above-mentioned shortcomings of the prior art, the main objective of the present invention is to provide a method and system for synthesizing a real-time image by using optical surface motion signals, aiming to solve the problem that the respiratory motion may induce a change in the position and shape of thoracic and abdominal tumors, producing off-target radiotherapy dose to cause recurrence or normal organ damage, which cannot be solved by the prior art.

An embodiment of the present invention provides a system for synthesizing a real-time image by using optical surface motion signals, including; an acquisition unit configured to acquire an image of a patient before treatment and real-time optical surface data of the patient during treatment; and a synthesis unit configured to synthesize the acquired image of the patient before treatment and the real-time optical surface data of the patient during treatment into a real-time image that is synchronized with a change of the optical surface motion signals according to a certain mapping relationship.

In some embodiments, the acquired image of the patient before treatment is a 4D image acquired directly before treatment, or a 4D image reconstructed from a three-dimensional (3D) image of the patient before treatment.

In some embodiments, the real-time optical surface data is standardized prior to synthesizing the acquired image of the patient before treatment and the real-time optical surface data of the patient during treatment into the real-time image synchronized with the change of the optical surface motion signals according to the certain mapping relationship.

In some embodiments, the system further includes a deep learning network model unit with the mapping relationship. The deep learning network model unit is configured to obtain an image of the patient at a certain phase i before treatment and optical surface data of the patient at a phase j during treatment, inputting a deep learning network model, outputting an image at the phase j, and combining images at continuous phases j, to obtain a real-time dynamic 4D image synchronized with the change of the optical surface motion signals.

An embodiment of the present invention provides a method for synthesizing a real-time image by using optical surface motion signals, including: acquiring an image of a patient before treatment and real-time optical surface data of the patient during treatment; and synthesizing the acquired image of the patient before treatment and the real-time optical surface data of the patient during treatment into a real-time image synchronized with a change of the optical surface motion signals according to a certain mapping relationship.

In some embodiments, the acquired image of the patient before treatment is a 4D image acquired directly before treatment, or a 4D image reconstructed from a 3D image of the patient before treatment.

In some embodiments, the real-time optical surface data is standardized prior to synthesizing the acquired image of the patient before treatment and the real-time optical surface data of the patient during treatment into the real-time image synchronized with the change of the optical surface motion signals according to the certain mapping relationship.

In some embodiments, the mapping relationship is obtained by a deep learning network model; and the method further includes: obtaining an image of the patient at a certain phase i before treatment and optical surface data of the patient at a phase j during treatment, inputting the deep learning network model, outputting an image at the phase j, and combining images at continuous phases j to obtain a real-time dynamic 4D image synchronized with the change of the optical surface motion signals.

An embodiment of the present invention provides a deep learning network model training system for synthesizing a real-time image by using optical surface motion signals, including a deep learning network model unit configured to train the deep learning network model to obtain a mapping relationship between body surface data and internal structure data of the patient. The deep learning network model is trained on a 4D image data set, an input of the deep learning network model includes the 4D image at the certain phase i and optical surface data or body surface outer contour data at another phase j, and an output of the deep learning network model is the image at the phase j.

An embodiment of the present invention provides a deep learning network model training method for synthesizing a real-time image by using optical surface motion signals, including: training the deep learning network model and obtaining the mapping relationship between the body surface data and the internal structure data of the patient. The deep learning network model is trained on a 4D image data set, an input of the deep learning network model includes the 4D image at the certain phase i and optical surface data or body surface outer contour data at another phase j, and an output of the deep learning network model is the image at the phase j.

The advantages of the technical solutions of the present invention are as follows. In the present invention, the deep learning technology is employed to mine and analyze a large number of 4D images of the patient before treatment, such as 4D-CBCT, 4D-CT, 4D-MR, and other internal motion images, and to correlate these 4D images with the characteristics of the optical surface respiratory motion signals during treatment to establish a dynamic mapping relationship. Then, the real-time 4D CBCT image is synthesized by using the CBCT image before treatment and the synchronized optical surface motion signals during treatment. A dynamic mapping model between 3D/4D image anatomical information and the characteristics of the optical surface motion signals is established based on the deep learning technology and multi-modal medical big data with moving target tracking as the main goal, thereby achieving real-time, non-invasive and dynamic visual monitoring of the internal structures of the internal moving target volumes. In this way, the present invention provides a real-time monitoring scheme for moving target volumes with a lower economic cost, wider application range of patients, better compatibility with existing medical facilities and traditional quality control equipment, thus improving the accuracy and effective, active period of radiotherapy for moving target volumes, and reducing the risk of tumor recurrence and metastasis and normal tissue radiation damage caused by off-target.

BRIEF DESCRIPTION OF THE DRAWINGS

The present invention will be further explained in the form of illustrative embodiments, described in detail with reference to the drawings. These embodiments are non-restrictive. In these embodiments, the same reference numeral represents the same structure.

DETAILED DESCRIPTION OF THE EMBODIMENTS

In order to explain the technical solutions of the embodiments of the present invention more clearly, the drawings used in the description of the embodiments will be briefly introduced below. Obviously, the drawings in the following description are only some examples or embodiments of the present invention, and the technical features of the various embodiments can be combined with each other to form a practical solution to achieve the objective of the present invention. For those having ordinary skill in the art, the present invention can also be applied to other similar scenarios based on these drawings without creative efforts. Unless it is obvious from the language environment or otherwise explained, the same reference numerals in the figures represent the same structure or operation.

It should be understood that the terms "system" and "unit" used herein are intended to distinguish different components, elements, parts, parts, or assemblies of different levels. However, if other terms can achieve the same purpose, they can be replaced by other expressions. In addition, the "system" and "unit" can be implemented by software or hardware, and can be designated as physical or virtual parts with the function part. The flow chart is used in the present invention to illustrate the operations performed by the system according to the embodiments of the present invention. It should be understood that the preceding or following operations are not necessarily performed exactly in order. Instead, the steps can be processed in reverse order or simultaneously. Also, other operations can be added to these processes, or a certain step or several operations can be removed from these processes. The technical solutions in the various embodiments can be combined with each other to achieve the objective of the present invention.

Embodiment 1

Figure 1:
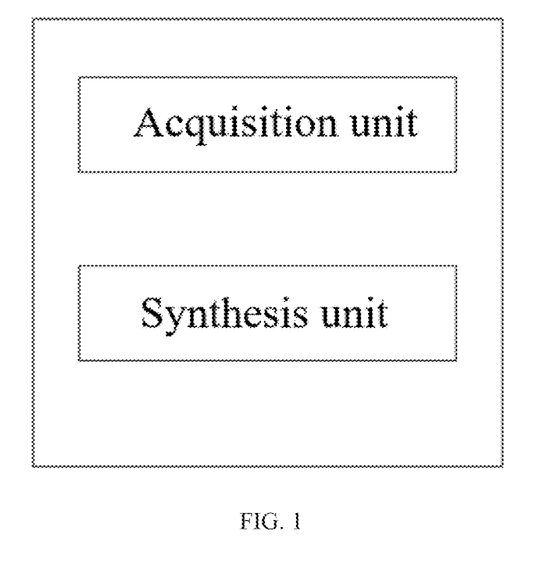
FIG. 1 is a schematic diagram of a system for synthesizing the real-time image by using the optical surface motion signals according to some embodiments of the present invention.
Figure 2:
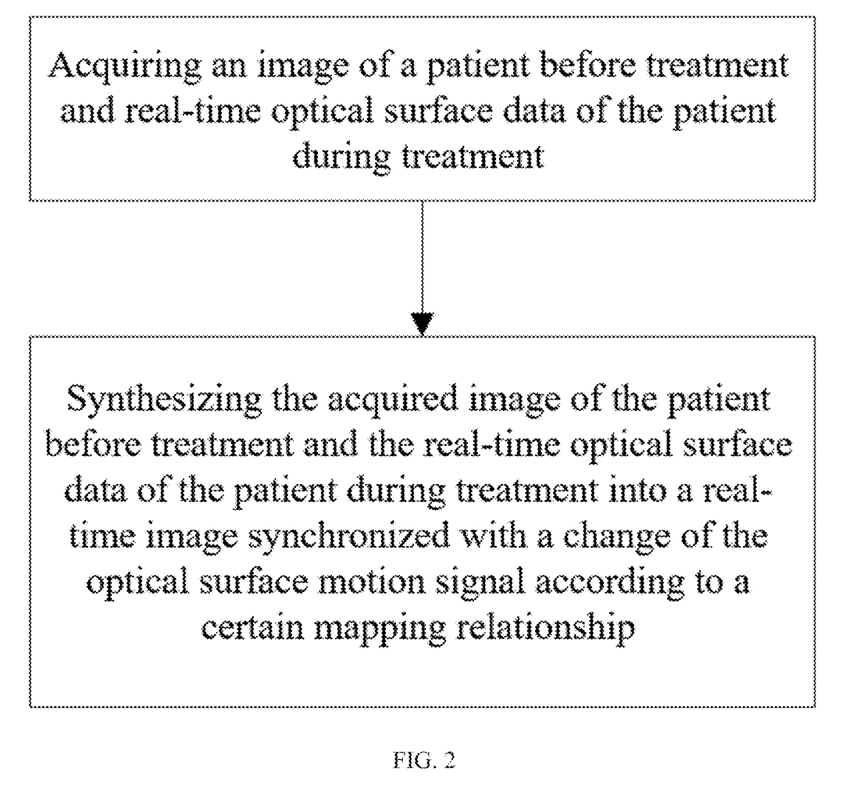
FIG. 2 is a flow chart of the method for synthesizing the real-time image by using the optical surface motion signals according to some embodiments of the present invention.

As shown in FIG. 1, a system for synthesizing a real-time image by using optical surface motion signals includes: an acquisition unit configured to acquire an image of a patient before treatment and real-time optical surface data of the patient during treatment; a synthesis unit configured to synthesize the acquired image of the patient before treatment and the real-time optical surface data of the patient during treatment into a real-time image that is synchronized with a change of the optical surface motion signals according to a certain mapping relationship.

To optimize the image of the patient before treatment, it is recommended to take the image immediately before when the patient starts treatment.

The acquired image of the patient before treatment, the method includes but not limited to, acquiring a 4D-CBCT image of the patient before treatment, note that other means may also be used to acquire the 4D image, for example, the 4D image before treatment can also be reconstructed from 2D, 3D images obtained right before treatment using anatomy knowledge from simulation 4D image such as a simulation 4D-CT image or 4D-MRI image.

The optical surface data is the patient's body surface data collected by an optical body surface imaging system or other means. In an embodiment, the body surface is divided into meshes, such as triangular meshes, quadrilateral meshes, etc., to obtain coordinate data of each point on the meshes.

One embodiment according to the present invention includes an optical body surface imaging system. The LED light is projected onto the patient's body surface, and then the reflected light of the patient's body surface is obtained by a camera. The dynamic 3D body surface information is generated by the real-time reflected light. 3D body surface reconstruction is based on the principle of triangulation and can be used to calculate the patient's real-time six-dimensional body surface motions, including, the translational motion—the front and back, left and right, up and down sides; and the rotation motion-around the x-axis, around the y-axis, and around the z-axis.

In one embodiment according to the present invention, (1) a 4D-CBCT image of the patient before treatment is acquired; alternatively, a 4D image before treatment is reconstructed by taking the original kV 2D projections of 3D-CBCT and performing data processing using each phase data of a simulation 4D-CT image or 4D-MRI image;

(2) the optical surface data at time t is collected in real time during the treatment, and standardized into a 3D body surface binary mask or a 2D body surface height map, or other standard data formats; and (3) by using the 4D-CBCT image of the target patient before the treatment or the 4D fusion image obtained by reconstruction as well as the real-time optical body surface standardized data during the treatment, a synthetic real-time dynamic 4D-CBCT image using the change of the optical surface motion signals is obtained according to a certain mapping relationship.

In the present invention, the 4D images and other internal motion images that are reconstructed by the 4D-CBCT, 4D-CT, 4D-MR or 3D images of the patient before the treatment are correlated with the characteristics of the optical body surface 4D respiratory motion signal to establish a dynamic mapping relationship. Then, a real-time 4D CBCT image is synthesized by using the CBCT image before treatment and the synchronized optical surface motion signals during treatment, thereby realizing real-time, non-invasive, and dynamic visual monitoring of internal structures of the internal moving target volume. Based on the universal accelerator platform, the present invention provides a real-time monitoring scheme for moving target volumes with lower economic costs, wider range of patients, and better compatibility with existing medical facilities and traditional quality control equipment, which improves the accuracy and effective, active period of radiotherapy for moving target volumes, and reduces the risk of tumor recurrence and metastasis, and normal organ radiation damage caused by off-target.

Embodiment 2

The acquired image of the patient before treatment is a 4D image acquired directly before treatment, or from a 4D image reconstructed from a 3D image of the patient before treatment.

The acquired 4D image of the patient before treatment includes a 4D-CBCT, 4D-CT, 4D-MR image, etc., that can be directly used to construct multi-modal 4D image training dataset before treatment.

3D-CBCT is more common in clinic, and it also contains a large amount of useful information including anatomical structural changes of patients. A 4D image before treatment is reconstructed by taking the original kV 2D projections of 3D-CBCT and using each phase data of a 4D image, such as a simulation 4D-CT or 4D-MRI image.

In one of the illustrative embodiments of the present invention, the instantaneous kV 2D projections raw data of 3D-CBCT are associated with the motion signal of 4D-CT. The patient's 4D-CT prior anatomy is used to make up for the insufficient number of instantaneous kV 2D projections while retaining the anatomical information reflected by the kV 2D projections on the day of treatment, or the closest to the day of treatment. The specific method is as follows. First, a certain phase of 4D-CT is taken as the reference ($I_0$), then the new image can be expressed as:

$$I(I,j,k)=F(I_0,D)=I_0(i+D_x(I,j,k),j+D_y(I,j,k),k+D_z(I,j,k));$$

wherein, (I, j, k) represents the voxel position, D represents the deformation of the new image I relative to $I_0$, and $D_x$, $D_y$, and $D_z$ represent the components of the deformation D in the x, y, and z directions, respectively. Determine the deformations between each phase of 4D-CT and $I_0$, determine the average deformation $\overline{D}$, and perform a principal component analysis to obtain the first three principal components $D_1$, $D_2$, and $D_3$ of these deformations, then simplify the deformation D of I relative to $I_0$ as:

$$D=\overline{D}+w_1D_1+w_2D_2+w_3D_3,$$

wherein, $W_1$, $W_2$ and $W_3$ represent the weights of the principal components. The kV 2D projections (P) at a certain phase is searched, then the deformation of the 4D image at this phase relative to $I_0$ should satisfy: DRR (F($I_0$, D))=P, wherein, DRR represents a digital reconstructed projection of 1. The equation can be solved by gradient descent to obtain the weights of the principal components of each deformation to obtain the estimation of the 4D images. Subsequent B-spline basis can be used to fine-tune the deformation to make I have better consistency with the kV 2D projections at the same phase.

Alternatively, a 4D-MRI image can also be correlated with the instantaneous kV 2D projections of 3D-CBCT to obtain the 4D image, so as to obtain the real 4D anatomy of the patient close to that of the patient during treatment with the aid of good soft tissue resolution information of 4D-MRI.

The real-time optical surface data is standardized prior to synthesizing the acquired image of the patient before treatment and the real-time optical surface data during treatment into the real-time image synchronized with the change of the optical surface motion signals according to a certain mapping relationship.

Figure 3:
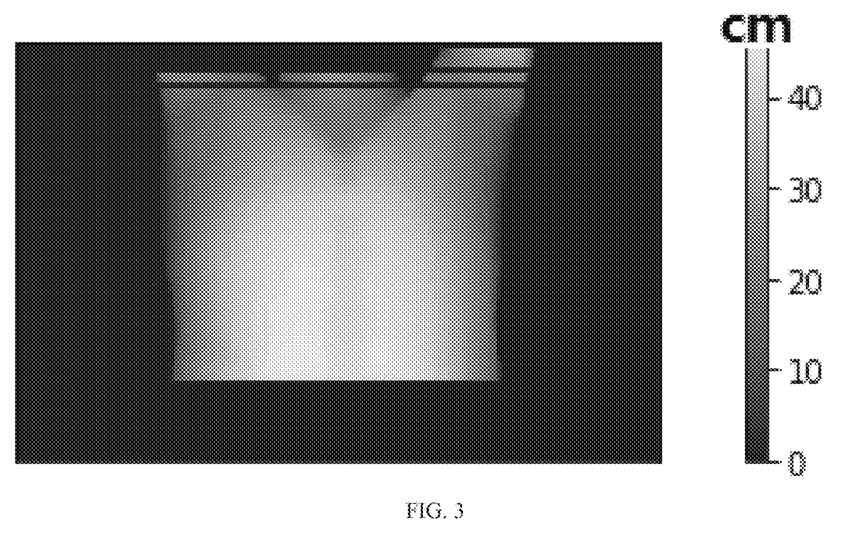
FIG. 3 is a two-dimensional (2D) height map obtained from the optical surface signal according to some embodiments of the present invention.
Figure 4:
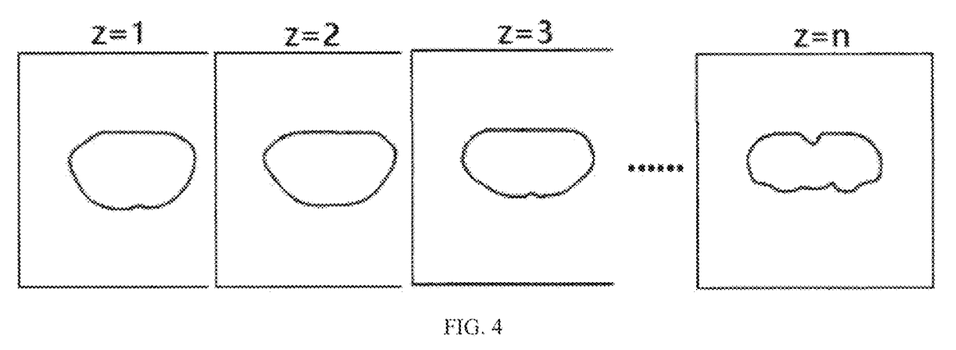
FIG. 4 is a 3D body surface binary mask obtained from the optical surface signal according to some embodiments of the present invention.

The patient's CT, MR, or CBCT images generally store the voxel distribution within the 3D rectangular coordinate system according to the Digital Imaging and Communications in Medicine (DICOM) standard. The optical body surface imaging system triangulates the body surface image collected by the sensor into triangulated data, and the distribution of triangle elements varies greatly with the patient's type. The deep learning neural network does not strictly limit the size, direction and resolution of the input image, but it requires a unified basic format of input data. The network trained in the present invention requires the body surface data as the input. In order to facilitate subsequent model training, the optical surface data and the body surface outer contour data extracted from CBCT image data are converted into standardized data for association. The body surface data is to be standardized as the 2D height distribution of each point on the body surface relative to the coronal plane where the isocenter is located, as shown in FIG. 3, or the 3D binary mask of the body surface contour as shown in FIG. 4, and both of which can be used as input data for the deep learning neural network.

The method of converting DICOM data into standardized data is to program the Python-based tools that process medical images using python library such as Pydicom, SimpleITK and Sickit-Image packages with similar functions, extract the CONTOUR DATA tags in DICOM to obtain the margin of the body surface, obtain the points within the margin using a polygon algorithm, and calculate distance of each point on the body surface to the isocenter along the direction perpendicular to the coronal plane to obtain the 2D height distribution of the body surface, or directly generate a 3D body surface binary mask.

The method of standardizing the optical surface signals is to project the vertex of the triangle element onto the coronal plane where the isocenter is located, obtain the height of the body surface at the projection according to the point coordinates, then interpolate to the entire plane to obtain the 2D height distribution map, and demarcate the body surface margin on each slice according to the body surface height to further generate the 3D binary mask of the body surface.

The system further includes a deep learning network model unit with the mapping relationship. The deep learning network model unit is configured to obtain an image of the patient at a certain phase i before treatment and optical surface data of the patient at a phase j during treatment (j≠i), inputting the deep learning network model, outputting an image at the phase j, and combining images at continuous phases j to obtain a real-time dynamic 4D image synchronized with the change of the optical surface motion signals.

The 4D-CBCT image of the patient scanned before treatment and the optical surface data of the patient collected in real time during treatment are standardized and used as the input of the deep learning network model to obtain a synthetic real-time dynamic 4D-CBCT image synchronized with the optical surface motion signals. For the patient with only a conventional 3D-CBCT image, a 4D image reconstructed by the kV 2D projections combined with 4D-CT or 4D-MRI is used as the substitute data of a 4D-CBCT image and input into the deep learning network model. In this way, a synthetic real-time dynamic 4D-CBCT image synchronized with the optical surface motion signals is also obtained.

The deep learning network model is set locally at the treatment end of the system that uses the optical surface motion signals to synthesize real-time images, or at the server end, or in the cloud. The deep learning network model is a trained model, or a continuously self-learning network model based on continuously updated 4D-CBCT images and optical surface data.

In the present invention, the deep learning technology is employed, whereby a large number of patients' 4D-CBCT, 4D-CT, 4D-MR and other internal motion images before treatment are mined and analyzed, and correlated with the characteristic of the 4D respiratory motion signal of the optical body surface during treatment to establish a dynamic mapping relationship, thereby synthesizing real-time 4D CBCT images by using the CBCT images before treatment and the synchronized optical surface motion signals during treatment.

Embodiment 3

A method for synthesizing the real-time image by using the optical surface motion signals has a one-to-one correspondence with the system for synthesizing the real-time image by using the optical surface motion signals, and the embodiment thereof can refer to Embodiment 1 to Embodiment 2.

Embodiment 4

Figure 5:
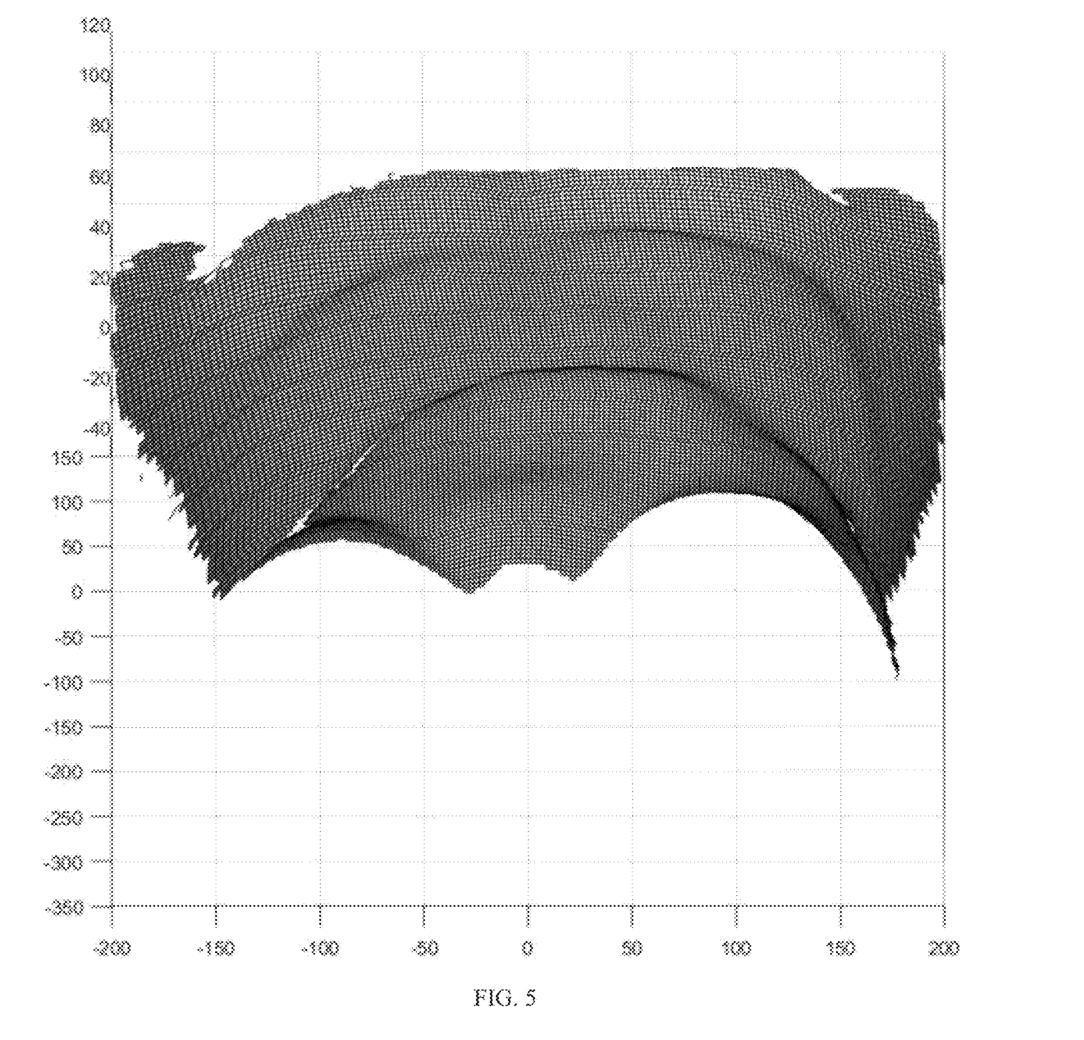
FIG. 5 depicts a body surface contour reconstructed by an optical body surface imaging system according to some embodiments of the present invention.
Figure 6:
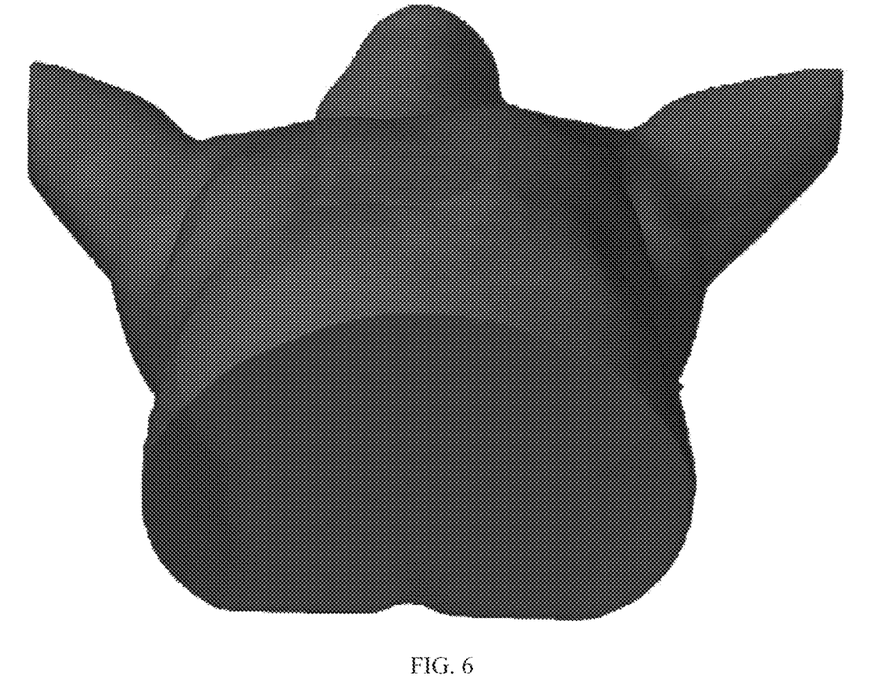
FIG. 6 depicts an image of a body surface outer contour obtained by a CT image delineation according to some embodiments of the present invention.
Figure 7:
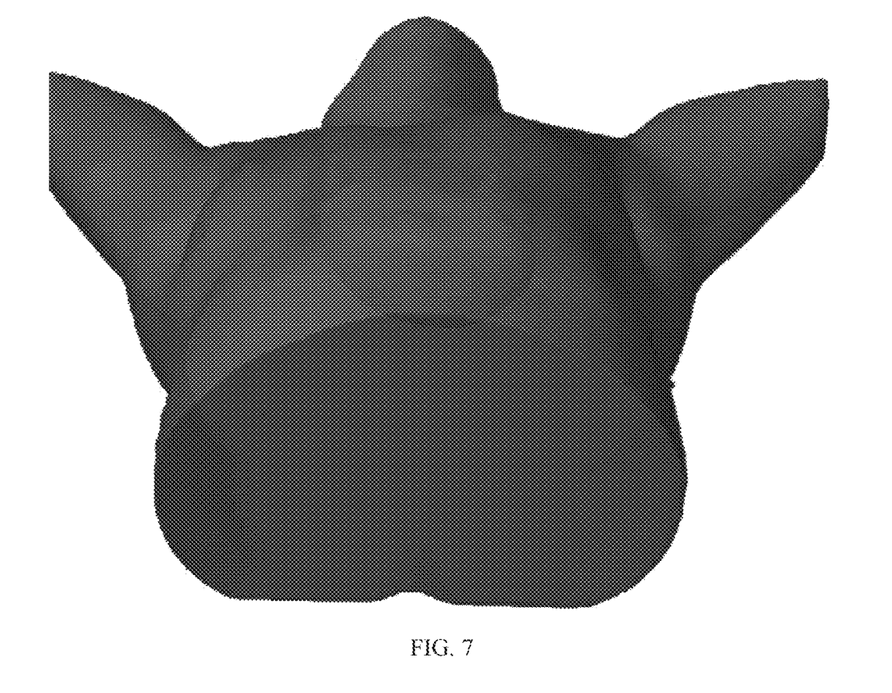
FIG. 7 depicts an image of the position information of the heart relative to the body surface of a patient at the imaging phase of FIG. 7 according to some embodiments of the present invention.
Figure 8:
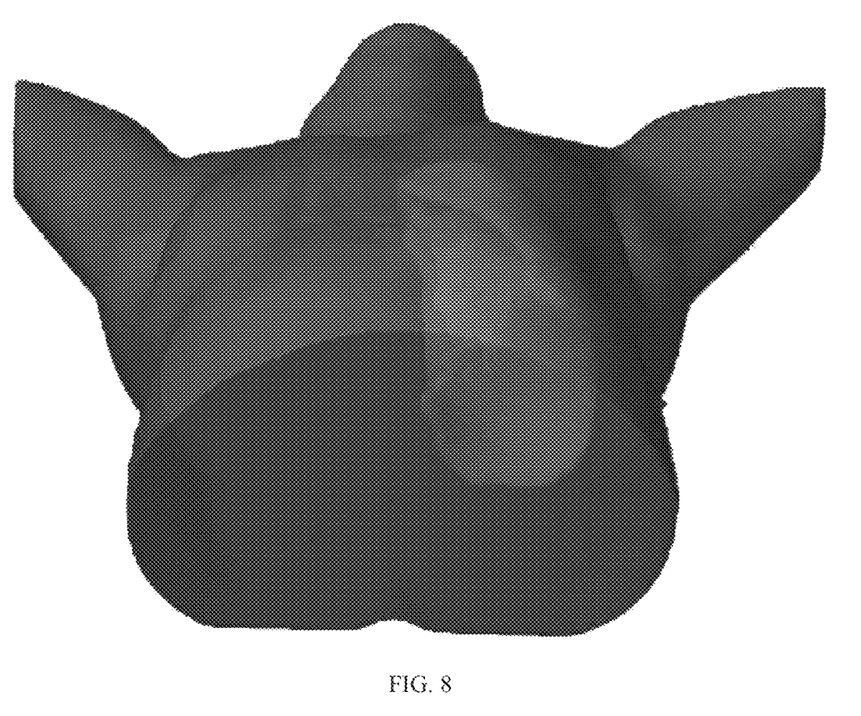
FIG. 8 depicts an image of the position information of the left lung relative to the body surface of the patient at the imaging phase of FIG. 7 according to some embodiments of the present invention.

A deep learning network model training system for synthesizing a real-time image by using optical surface motion signals includes a deep learning network model unit configured to train a deep learning network model to obtain a mapping relationship between body surface data and internal structure data of a patient. The deep learning network model is trained on a 4D image data set. The input of the deep learning network model includes a 4D image at the certain phase i and optical surface data or body surface outer contour data at another phase j, and the output of the deep learning network model is the image at the phase j. FIGS. 5-8 show the simulation 4D CT images of a patient at a certain phase and the corresponding real-time body surface information obtained through the optical body surface system during treatment. FIG. 5 depicts a body surface contour reconstructed by an optical body surface system. FIG. 6 depicts an image of a body surface outer contour obtained by a CT image delineation. FIG. 7 depicts an image of the position information of the heart relative to the body surface of a patient at the imaging phase of FIG. 7. FIG. 8 depicts an image of the position information of the left lung relative to the body surface of the patient at the imaging phase of FIG. 7.

Data preprocessing of the deep learning network model training set is as follows:

(1) A large number of 4D-CBCT, 4D-CT, 4dD-MR and other internal motion images of the patient before treatment are mined and analyzed. Alternatively, in order to make full use of the large amount of useful data contained in conventional 3D-CBCT, and to extend the application range of the model, a multi-modal 4D fusion image training set before treatment is constructed by using the patient's 4D-CT (incorporating 4D-MRI if available) prior anatomy, and anatomical information that is reflected by the kV 2D projections and collected during CBCT scanning on the day of treatment.

4D-CT, 4D-MR and 4D-CBCT can be directly used to construct multi-modal 4D image training set data before treatment. The more common clinical 3D-CBCT also contains massive useful information such as patients' anatomical changes. In order to overcome the averaging effect of the longer imaging time of 3D-CBCT on motion, in the present embodiment, the instantaneous kV 2D projections raw data of CBCT are correlated with the motion model of 4D-CT. The patient's 4D-CT prior anatomy is used to make up for the insufficient number of instantaneous kV 2D projections, while the anatomical information reflected by the kV 2D projections on the day of treatment is retained. The specific method for reconstructing a 4D image from a 3D image may adopt the method of Embodiment 2.

(2) The optical surface data of different patients or the body surface contour data extracted from CBCT image data are transformed into standardized data as the input data of the deep learning model. The optical surface data is obtained by dividing the body surface into meshes to obtain coordinate data of each point on the meshes. The outer contour data of the body surface is the outer contour data of the skin on the 3D or 4D image.

The patient's CT, MR, or CBCT images generally store the voxel distribution within the 3D rectangular coordinate system according to the DICOM standard. The optical body surface imaging system triangulates the body surface image collected by the sensor into triangulated data, and the distribution of triangle elements varies greatly with the patient's type. The deep learning neural network does not strictly limit the size, direction and resolution of the input image, but also requires a unified basic format of input data. The network trained in the present invention requires the body surface data as the input. In order to facilitate subsequent model training, the optical surface data and the body surface outer contour data extracted from CBCT image data are converted into standardized data for association. The body surface data is to be standardized as the 2D height distribution of each point on the body surface relative to the coronal plane where the isocenter is located, as shown in FIG. 3, or the 3D binary mask of the body surface contour as shown in FIG. 4, and both of which can be used as input data for the deep learning neural network.

The method of converting DICOM data into standardized data is to program the Python-based tools that process medical images using python library such as Pydicom, SimpleITK and Sickit-Image packages with similar functions, extract the CONTOUR DATA tags in DICOM to obtain the margin of the body surface, obtain the points within the margin using a polygon algorithm, and calculate distance of each point on the body surface to the isocenter along the direction perpendicular to the coronal plane to obtain the 2D height distribution of the body surface, or directly generate a 3D body surface binary mask. The method of standardizing the optical surface signals is to project the vertex of the triangle element onto the coronal plane where the isocenter is located, obtain the height of the body surface at the projection according to the point coordinates, then interpolate to the entire plane to obtain the 2D height distribution map, and demarcate the body surface margin on each slice according to the body surface height to further generate the 3D binary mask of the body surface.

More abundant real-time dynamic spatial data can be obtained by directly reconstructing the skin 4D optical body surface. For example, the Catalyst (C-Rad, Sweden) and other systems used in the present embodiment can achieve submillimeter body surface positioning accuracy and long-term stability, and support six-degree-of-freedom non-rigid registration. Although the system is still subject to the accuracy limitation and individual differences of the indirect body surface signal itself, a large number of 4D body surface motion data of the patient are combined with other multi-modal 4D internal dynamic images via the deep learning technology to provide more abundant and accurate correlation features for the construction of the body surface-internal synchronous dynamic mapping model.

Construction and application of the deep learning network model: The deep learning model of the 4D fusion image data set is improved by adding a layer of input, that is, the standardized data of body surface characteristics, and then retrained on the above 4D fusion image data set to construct a generative model to dynamically map the optical surface motion signals with the internal anatomy contained in the fusion image.

Model Training Stage:

The existing deep learning network model for image generation is improved by adding a layer of input, that is, the body surface standardized data, and then retrained on the 4D fusion image data set. The input of the deep learning network model is a fusion image at a certain phase (such as the phase i) and a 3D body surface binary mask or 2D body surface height map at another phase j (j≠i), and the output of the deep learning network model is a 3D-CBCT image at the phase j (mainly to ensure an accurate position of the target volume). The loss function adopts the sum of squared deviations with the L1 regularization penalty, and the model parameters are iteratively optimized according to the gradient of the loss function. The output of the model is the synthetic real-time dynamic 4D-CBCT image using the change of the optical surface motion signals.

The deep learning network model adopted in the present embodiment includes three gradually progressive models, including a U-net convolutional neural network, a generative adversarial network (GAN), and a deep recurrent neural network to makes full use of the advantages and characteristics of various models. The U-net convolutional neural network is a relatively simple image generation network, which adopts a U-net architecture. There are jump links in the Downsampling and Upsampling layers at both ends, so that the model can make full use of the multi-scale features of the image. The output of the model is an image with the same size as that of the input image. The GAN uses two convolutional neural networks as an image generator and a classifier, respectively, and the prediction effect of the generator is improved through the antagonism of the two convolutional neural networks. In the present invention, the trained U-net convolutional neural network is used as the generator of the GAN model, and an additional convolutional neural network is used as the classifier to improve the prediction effect of the model. Based on this, the deep recurrent neural network can be further used to mine the correlations between different phases to solve the problems associated with time series signals. In this model, the output at a certain time is used as one of the inputs at the next time or several times later and affect the output of the neural network at this phase, thereby extracting the self-correlation information of the time series signal. After a more complete image generation network is obtained through the training of the first two models, the body surface data can be used as a periodic signal and input, and the image can be used as one of the inputs at the next time. The CBCT image output at each time will be used as one of the inputs at the next time.

Embodiment 5

A deep learning network model training method for synthesizing the real-time image by using the optical surface motion signals has a one-to-one correspondence with the deep learning network model training system for synthesizing the real-time image by using the optical surface motion signals, and the specific description thereof can refer to Embodiment 4.

In the technical solution of the present invention, the results of the obtained synthetic real-time dynamic 4D-CBCT image using the change of the optical surface motion signals are verified by the following methods, which are accurate, real-time and reliable, and can be applied to conventional radiotherapy.

(1) The 4D extended cardiac-torso (XCAT) digital phantom is employed to simulate the patient's normal/abnormal breathing pattern, anatomy and motion changes by setting different parameters in the software, so as to generate virtual patient images corresponding to different imaging modalities (4D-CT, 4D-MRI and 4D-CBCT) and then applied them to the model to preliminarily verify the accuracy of the model.

(2) The optical surface signal and the 4D-CBCT data of the simulated motion phantom are synchronously collected. The 4D-CT and 4D-MRI data of the same phantom are used as the model input, and the synthesized 4D-CBCT image output from the model is compared with the known 4D-CBCT data at the same phase to evaluate the accuracy of the method. The respiratory phase setting of the phantom is adjusted. The simulated motion phantom can also input real breathing patterns of different patients to better simulate complex clinical scenes, and the accumulated data can be used as a supplement to the model training set.

(3) The navigation gold standard (Beacon) is implanted in the motion plug-in of the simulated phantom. The Beacon radio frequency wave position tracked by the Calypso real-time positioning system, or the real-time gold standard position obtained by fluoroscopy imaging (simulating an ordinary gold standard implantation without radio frequency wave emission function) is taken as a reference to evaluate the accuracy and sensitivity of the synthesized 4D-CBCT image in monitoring the position of the moving target volume.

The above verification results are used as feedback data to further debug and iteratively optimize the model.

The applicant serves in a large modern grade-A tertiary specialist tumor hospital integrating clinic, scientific research, teaching and prevention, that is, the Peking University Cancer Hospital, admitting 730,000 outpatient visits in 2019. While providing patients with first-class tumor diagnosis and treatment services, with the support of the Key Laboratory of Malignant Tumor Pathogenesis and Translational Research of the Ministry of Education, an advanced multi-modal medical database and interdisciplinary research collaboration platform have been established to provide sufficient cases for this project and data resources for model training and verification. The pre-experimental data preliminarily supports the technical solution of the present invention, exhibiting good overall feasibility. Based on the data of 500 patients accepted thoracic radiotherapy using the optical body surface guidance system during treatment, the patient's simulation 4D CT image and optical body surface information derived from the optical body surface in real-time are used to verify that the body surface motion and the internal structure motion have a good mapping relationship, the accuracy thereof reaches over 95%, and the expected effect of mapping the changes in the internal anatomy through body surface motion is achieved.

The embodiments of the present invention have at least the following possible advantages. In the present invention, the deep learning network model is trained by fusing multi-modal medical big data, the individualized dynamic mapping relationship between the body surface signal characteristics and the position of the internal moving target volume is established, and then the real-time dynamic 4D-CBCT image synchronized with the optical surface motion signals is synthesized by using the CBCT image before treatment and the optical surface motion signals during treatment, which guides the monitoring of moving target volumes in precise radiotherapy, and provides medical evidence-based and scientific methods for clinical decision-making. Compared with the traditional 4D-imaging, the 4D-CBCT synthesized by the artificial intelligence technology of the present invention closely represent the real anatomy and respiratory motion of the patient during treatment. The synthesized real-time 4D-CBCT can be used as a complementary technology for complex integrated devices such as MR-accelerators to achieve precise, real-time, non-invasive, visual dynamic tracking of the moving target volumes without concomitant dose during radiotherapy on the existing traditional accelerator platform, which has the advantages of low cost, good compatibility and universal applicability, and is conducive to clinical promotion and industrial application.

It should be noted that different embodiments may have different advantages. In different embodiments, the possible advantages can be any one or a combination of the above advantages, or any other advantages that may be obtained.

The basic concepts have been described above. Obviously, for those skilled in the art, the above detailed disclosure is only illustrative and does not constitute a limitation of the present invention.

In addition, unless explicitly stated in the claims, the order of processing elements and sequences, the use of numbers and letters, or the use of other designations in the present invention are not used to limit the order of the processes and methods of the present invention. Although the foregoing disclosure uses various examples to discuss some embodiments of the present invention that are currently considered useful, it should be understood that such details are only for illustrative purposes, and the appended claims are not limited to the disclosed embodiments. Instead, the claims are intended to cover all modifications and equivalent combinations that conform to the spirit and scope of the embodiments of the present invention.

Similarly, it should be noted that in order to simplify the description of the disclosure of the present invention to facilitate the understanding of one or more embodiments of the invention, in the foregoing description of the embodiments of the present invention, various features are sometimes combined into one embodiment, drawings, or description thereof. However, the method of disclosure does not mean that the object of the present invention requires more features than those mentioned in the claims.

Finally, it should be understood that the embodiments described in the present invention are only used to illustrate the principles of the embodiments of the present invention. Other modifications may also fall within the scope of the present invention. Therefore, as an example rather than a limitation, alternative configurations of the embodiments of the present invention can be considered as consistent with the teachings of the present invention. Accordingly, the embodiments of the present invention are not limited to the embodiments explicitly introduced and described in the present invention.

What is claimed is:

1. A system for synthesizing a real-time image by using optical surface motion signals, comprising: an acquisition unit and a synthesis unit; wherein
   the acquisition unit is configured to acquire an image of a patient before a treatment and real-time optical surface data of the patient during the treatment; and
   the synthesis unit is configured to implement a synthesizing of the image of the patient before the treatment and the real-time optical surface data of the patient during the treatment into the real-time image synchronized with a change of the optical surface motion signals according to a mapping relationship, wherein the real-time optical surface data and the optical surface motion signals are measurements of a movement of a surface of the patient's body obtained from optical light.

2. The system according to claim 1, wherein,
   the image of the patient before the treatment is a 4D image acquired directly before the treatment, or a LID image reconstructed from a 3D image of the patient before the treatment.

3. The system according to claim 2, further comprising a deep learning network model unit with the mapping relationship; wherein
   the deep learning network model unit is configured to obtain the image of the patient at a first phase before the treatment and the real-time optical surface data of the patient at a second phase during the treatment, input a deep learning network model, output an image at the second phase, and combine images at continuous phases to obtain a real-time dynamic 4D image synchronized with the change of the optical surface motion signals.

4. The system according to claim 1, wherein,
   the real-time optical surface data is standardized prior to synthesizing the image of the patient before the treatment and the real-time optical surface data of the patient during the treatment into the real-time image synchronized with the change of the optical surface motion signals according to the mapping relationship.

5. The system according to claim 4, further comprising a deep learning network model unit with the mapping relationship; wherein
   the deep learning network model unit is configured to obtain the image of the patient at a first phase before the treatment and the real-time optical surface data of the patient at a second phase during the treatment, input a deep learning network model, output an image at the second phase, and combine images at continuous phases to obtain a real-time dynamic 4D image synchronized with the change of the optical surface motion signals.

6. The system according to claim 1, further comprising a deep learning network model unit with the mapping relationship; wherein
   the deep learning network model unit is configured to obtain the image of the patient at a first phase before the treatment and the real-time optical surface data of the patient at a second phase during the treatment, input a deep learning network model, output an image at the second phase, and combine images at continuous phases to obtain a real-time dynamic 4D image synchronized with the change of the optical surface motion signals.

7. The system of claim 1, wherein said synthesizing into the real-time image is performed by employing body surface outer contour data, extracted from said image of the patient before the treatment and the real-time optical surface data, and wherein the body surface outer contour data and the real-time optical surface data are respectively defined as: a) a corresponding 2D height distribution of points of the surface of the patient's body relative to a coronal plane, or b) a corresponding 3D binary mask of a contour of the surface of the patient's body.

8. The system of claim 1, wherein said synthesizing into the real-time image is performed by employing body surface outer contour data extracted from said image of the patient before the treatment and the real-time optical surface data, and wherein the body surface outer contour data and the real-time optical surface data are respectively defined as a corresponding 2D height distribution of points of the surface of the patient's body relative to a coronal plane.

9. The system of claim 1, wherein said synthesizing into the real-time image is performed by employing body surface outer contour data extracted from said image of the patient before the treatment and the real-time optical surface data, and wherein the body surface outer contour data and the real-time optical surface data are respectively defined as a corresponding 3D binary mask of a contour of the surface of the patient's body.

10. A method for synthesizing a real-time image by using optical surface motion signals, comprising:
    acquiring an image of a patient before a treatment and real-time optical surface data of the patient during the treatment; and
    synthesizing the image of the patient before the treatment and the real-time optical surface data of the patient during the treatment into the real-time image synchronized with a change of the optical surface motion signals according to a mapping relationship, wherein the real-time optical surface data and the optical surface motion signals are measurements of a movement of a surface of the patient's body obtained from optical light.

11. The method according to claim 10, wherein,
    the image of the patient before the treatment is a 4D image acquired directly before the treatment or a 4D image reconstructed from a 3D image of the patient before the treatment.

12. The method according to claim 11, wherein,
the mapping relationship is obtained by a deep learning network model; and
the method further comprises:
obtaining the image of the patient at a first phase before the treatment and the real-time optical surface data of the patient at a second phase during the treatment,
inputting the deep learning network model,
outputting an image at the second phase, and
combining images at continuous phases to obtain a real-time dynamic 4D image synchronized with the change of the optical surface motion signals.

13. The method according to claim 10, further comprising standardizing the real-time optical surface data prior to synthesizing the image of the patient before the treatment and the real-time optical surface data of the patient during the treatment into the real-time image synchronized with the change of the optical surface motion signals according to the mapping relationship.

14. The method according to claim 13, wherein,
the mapping relationship is obtained by a deep learning network model; and
the method further comprises:
obtaining the image of the patient at a first phase before the treatment and the real-time optical surface data of the patient at a second phase during the treatment,
inputting the deep learning network model,
outputting an image at the second phase, and
combining images at continuous phases to obtain a real-time dynamic 4D image synchronized with the change of the optical surface motion signals.

15. The method according to claim 10, wherein,
the mapping relationship is obtained by a deep learning network model; and
the method further comprises:
obtaining the image of the patient at a first phase before the treatment and the real-time optical surface data of the patient at a second phase during the treatment,
inputting the deep learning network model,
outputting an image at the second phase, and
combining images at continuous phases to obtain a real-time dynamic 4D image synchronized with the change of the optical surface motion signals.

16. The method of claim 10, wherein said synthesizing into the real-time image is performed by employing body surface outer contour data extracted from said image of the patient before the treatment and the real-time optical surface data, and wherein the body surface outer contour data and the real-time optical surface data are respectively defined as:
a) a corresponding 2D height distribution of points of the surface of the patient's body relative to a coronal plane, or
b) a corresponding 3D binary mask of a contour of the surface of the patient's body.

17. The method of claim 10, wherein said synthesizing into the real-time image is performed by employing body surface outer contour data extracted from said image of the patient before the treatment and the real-time optical surface data, and wherein the body surface outer contour data and the real-time optical surface data are respectively defined as a corresponding 2D height distribution of points of the surface of the patient's body relative to a coronal plane.

18. The method of claim 10, wherein said synthesizing into the real-time image is performed by employing body surface outer contour data extracted from said image of the patient before the treatment and the real-time optical surface data, and wherein the body surface outer contour data and the real-time optical surface data are respectively defined as a corresponding 3D binary mask of a contour of the surface of the patient's body.

* * * * *